(12) United States Patent
Fukuda et al.

(10) Patent No.: US 6,451,969 B1
(45) Date of Patent: Sep. 17, 2002

(54) METHODS FOR INHIBITING TUMOR METASTASIS, AND PEPTIDES USEFUL THERFOR

(75) Inventors: Michiko Fukuda; Minoru Fukuda, both of San Diego, CA (US)

(73) Assignee: The Burnham Institute, La Jolla, CA (US)

( * ) Notice: Subject to any disclaimer, the term of this patent is extended or adjusted under 35 U.S.C. 154(b) by 0 days.

(21) Appl. No.: 09/232,484

(22) Filed: Jan. 15, 1999

(51) Int. Cl.$^7$ .......................... C07K 5/00; C07K 14/00; C07K 1/00; C07K 17/00

(52) U.S. Cl. ...................... 530/300; 530/345; 530/350; 530/402

(58) Field of Search ................................. 530/300, 350, 530/345, 402

(56) References Cited

U.S. PATENT DOCUMENTS

| | | |
|---|---|---|
| 4,631,211 A | 12/1986 | Houghten |
| 5,064,655 A * | 11/1991 | Uster et al. |
| 5,223,409 A | 6/1993 | Ladner et al. |
| 5,728,802 A | 3/1998 | Barrett et al. |

FOREIGN PATENT DOCUMENTS

WO    WO 98/53071    * 11/1998

OTHER PUBLICATIONS

Murakami, Y. et al. Analysis of the nucleotided sequence of chromosome VI from *Saccharomyces cerevisiae.* Nature Genetics, 10: 261–268, Jul. 1995.*

Accession No. Q57497, Database SPTREMBL, Everisss, K.D. et al., Nov. 1996.*

Heerze et al., "Utilization of sialic acid–binding synthetic peptide sequences derived from pertussis toxin as novel anti–inflammatory agents," *Glycobiology* 5(4):427–433 (1995).

Martens et al., "Peptides which bind to E–selectin and block neutrophil adhesion," *J. Biol. Chem.* 270(36):21129–21136 (1995).

Morikawa et al., "Treatment of focal cerebral ischemia with synthetic oligopeptide corresponding to lectin domain of selectin," *Stroke* 27(5):951–955 (1996).

Rozdzinski et al., "Prokaryotic peptides that block leukocyte adherence to selectins," *J. Exp. Med.* 178:917–924 (1993).

Stone et al., "P–selectin mediates adhesion of platelets to neuroblastoma and small cell lung cancer," *J. Clin. Invest.* 92:804–813 (1993).

Aboud–Pirak et al., "Cytotoxic Activity of Daunorubicin or Vindesin Conjugated to A Monoclonal Antibody on Cultured MCF–7 Breast Carcinoma Cells," *Biochem. Pharmacol.* 38:641–648 (1989).

Anostario et al., "A Ligand Binding Assay for E–Selectin," *Anal. Biochem.* 221:317–322 (1994).

Berg et al., "A Carbohydrate Domain Common to Both Sialyl Le$^a$ and Sialyl Le$^x$ Is Recognized by the Endothelial Cell Leukocyte Adhesion Molecule ELAM–1," *J. Biol. Chem.* 266:14869–14872 (1991).

Bevilacqua et al., "Endothelial Leukocyte Adhesion Molecule 1: An Inducible Receptor for Neutrophils Related to Complement Regulatory Proteins and Lectins," *Science* 243:1160–1165 (1989).

Bodansky M., *Principles of Peptide Synthesis* 2nd ed. (Springer–Verlag) 1988 and (1993 Supp.) Title page only.

Briand et al., "Application and limitations of the multiple antigen peptide (MAP) system in the production and evaluation of anti–peptide and anti–protein antibodies," *J. Immunol. Meth.* 156:255–265 (1992).

Dillman et al., "Significance of antigen, drug, and tumor cell targets in the preclinical evaluation of doxorubicin, methotrexate, and mitomycin–C monoclonal antibody immunoconjugates," *Mol. Biother.* 1:250–255 (1989).

Dyson et al., "The Physical Basis for Induction of Protein–Reactive Antipeptide Antibodies," *Ann. Rev. of Biophysics and Biophysical Chem.* 17:305–324 (1988).

Fitzpatrick and Garnett, "Studies on the mechanism of action of an MTX–HSA–MoAb conjugate, " *Anti–Cancer Drug Des.* 10:11–24 (1995).

Fitzpatrick and Garnett, "Design, synthesis and in vitro testing of methotrexate carrier conjugates linked via oligopeptide spacers," *Anti–Cancer Drug Des.* 10:1–9 (1995).

Goldman et al., "Targeted gene delivery to Kaposi's sarcoma cells via the fibroblast growth factor receptor$^1$," *Cancer Res.* 15:1447–1451 (1997).

Henn et al., "Synthesis of 2'—Deoxyuridine and 5–Fluoro–2'–deoxyuridine Derivatives and Evaluation in Antibody Targeting Studies," *J. Med. Chem.* 36:1570–1579 (1993).

Irimura et al., "Colorectal cancer metastasis determined by carbohydrate–mediated cell adhesion: role of sialyl–Le$^x$ antigens," *Cancer Biol.* 4:319–324 (1993).

Johnston et al., "Cloning of GMP–140, a Granule Membrane Protein of Platelets and Endothelium: Sequence Similarity to Proteins Involved in Cell Adhesion and Inflammation," *Cell* 56:1033–1044 (1989).

Kannagi R., "Carbohydrate–mediated cell adhesion involved in hematogenous metastasis of cancer," *Glycoconjugate J.* 4:577–584 (1997).

(List continued on next page.)

*Primary Examiner*—Anthony C. Caputa
*Assistant Examiner*—Karen A. Canella
(74) *Attorney, Agent, or Firm*—Campbell & Flores LLP

(57) ABSTRACT

In accordance with the present invention, there are provided peptides that bind to a member of the mammalian selectin family and inhibit the binding of a carbohydrate to the selectin. Invention peptides are useful to inhibit of the adhesion of cells containing particular cell-surface carbohydrates to cells containing cell-surface selecting. Also provided are pharmaceutical compositions comprising invention peptides useful in methods for inhibiting a carbohydrate from binding to a selectin, and in methods of inhibiting tumor cell metastasis in a subject.

34 Claims, 2 Drawing Sheets

OTHER PUBLICATIONS

Krauer et al., "Antitumor Effect of 2'–Deoxy–5–fluorouridine Conjugates against a Murine Thymoma and Colon Carcinoma Xenografts," *Cancer Res.* 52:132–137 (1997).

Kukowska–Latallo et al., "A cloned human cDNA determines expression of a mouse stage–specific embryonic antigen and the Lewis blood group α (1,3/1,4) fucosyltransferase," *Genes & Develop.* 4:1288–1303 (1990).

Laskey et al., "Cloning of a Lymphocyte Homing Receptor Reveals a Lectin Domain," *Cell* 56:1045–1055 (1989).

Martín–Satué et al., "Enhanced Expression of α(1,3)–Fucosyltransferase Genes Correlates with E–selectin–mediated Adhesion and metastatic Potential of Human Lung Adenocarcinoma Cells[1]," *Cancer Res.* 58:1544–1550 (1989).

McEver R.P., "Selectin–carbohydrate interactions durning inflammation and metastasis," *Glycoconjugate J.* 4:585–591 (1997).

Miyasaka M., "Cancer Metastasis and Adhesion Molecules," *Clin. Orthop.* 312:10–18 (1995).

Nakamori et al., "Increased Expression of Sialyl Lewis[x] Antigen Correlates with Poor Survial in Patients with Colorectal Carcinoma: Clinicopathological and Immunohistochemical Study[1]," *Cancer Res.* 53:3632–3637 (1993).

Nakashio et al., "The Association of Metastasis with the Expression of Adhesion Molecules in Cell Lines Derived from Human Gastric Cancer," *Anticancer Res.* 17:293–300 (1997).

Nelson et al., "Higher–Affinity Oligosaccharide Ligands for E–Selectin," *J. Clin. Invest.* 91:1157–1166 (1993).

Pelton et al., "Conformationally restricted analogs of somatostatin with high $\mu$–opiate receptor specificity," *Proc. Natl. Acad. Sci. USA* 82:236–239 (1985).

Rees et al., Protein Engineering: A Practical Approach IRL Press 1992 Table of contents only.

Rowland et al., "Preclinical investigation of the antitumour effects of anti–CD19–idarubicin immunoconjugates," *Cancer Immunol. Immunother.* 37:195–202 (1993).

Sato et al., "The Association of Sialyl Lewis[a] Antigen with the Metastatic Potential of Human Colon Cancer Cells," *Anticancer Res.* 17:3505–3512 (1997).

Sawada et al., "Differential E–selectin–dependent Adhesion Efficiency in Sublines of a Human Colon Cancer Exhibiting Distinct Metastatic Potentials," *J. Biol. Chem.* 269:1425–1431 (1994).

Schechter et al., "Indirect Immunotargeting of CIS–PT To Human Epidermoid Carcinoma KB Using the Avidin–Biotin System," *Int. J. Cancer* 48:167–172 (1991).

Schott et al., "Comparison of Linear and Branched Peptide Forms (MAPs) in the Induction of T Helper Responses to Point–Mutated ras Immunogens," *Cell Immun.* 174:199–209 (1996).

Shawler et al., "Preclinical Trials Using an Immunoconjugate of T101 and Methotrexate in an Athymic Mouse/Human T–Cell Tumor Model," *J. Biol. Resp. Mod.* 7:608–618 (1988).

Shih et al., "Internalization of an intact doxorubicin immunoconjugate," *Cancer Immunol. Immunother.* 38:92–98 (1994).

Sivam et al., "Therapeutic Efficacy of a Doxorubicin Immunoconjugate in a Preclinical Model of Spontaneous Metastatic Human Meloanoma[1]," *Cancer Res.* 55:2352–2356 (1995).

Smith et al., "Building Synthetic Antibodies as Adhesive Ligands for Integrins," *J. Biol. Chem.* 269:32788–32795 (1994).

Smyth et al., "The cellular uptake and cytotoxicity of chlorabucil–monoclonal antibody conjugates," *Immunol. Cell Biol.* 65:315–321 (1987).

Starling et al., "In Vivo Antitumor Activity of a Panel of Four Monoclonal Antibody–Vinca Alkaloid Immunoconjugates Which Bind to Three Distinct Epitopes of Carcinoembryonic Antigen," *Bioconj. Chem.* 3:315–322 (1992).

Sueyoshi et al., "Expression of Distinct Fucosylated Oligosaccharides and Carbohydrate–mediated Adhesion Efficiency Directed by Two Different α–1,3–Fucosyltransferases," *J. Biol. Chem.* 269:32342–32350 (1994).

Takada et al., "Adhesion of Human Cancer Cells to Vascular Endothelium Mediated by a Carbohydrate Antigen, Sialyl Lewis A[1]," *Biochem. Biophys. Res. Comm.* 179:713–719 (1991).

Takada et al., "Contribution of Carbohydrate Antigens Sialyl Lewis A and Sialyl Lewis X to Adhesion of Human Cancer Cells to Vascular Endothelium[1]," *Cancer Res.* 53:354–361 (1993).

Tedder et al., "Isolation and Chromosomal Localization of cDNAs Encoding A Novel Human Lymphocyte Cell Surface Molecule, LAM–1," *J. Exp. Med.* 170:123–133 (1989).

Tozeren et al., "E–selectin–mediated dynamic interactions of breast–and colon–cancer cells with endothelial–cell monolayers," *Int. J. Cancer* 60:426–431 (1995).

Weitz–Schmidt et al., "An E–Selectin Binding Assay Based on a Polyacrylamide–Type Glycoconjugate," *Anal. Biochem.* 238:184–190 (1996).

Welply et al, "Multivalent sialyl–LeX: potent inhibitors of E–selectin–mediated cell adhesion; reagent for staining activated endothelial cells," *Glycobiology* 4:259–265 (1994).

Wenzel et al., "Adhesion of Head and Neck Squamous Cell Carcinoma to Endothelial Cells," *Arch. Otolaryngol Head Neck Surg.* 121:1279–1286 (1995).

* cited by examiner

METHODS FOR INHIBITING TUMOR METASTASIS, AND PEPTIDES USEFUL THERFOR

This invention was funded in part by NIH Grant No. CA71932 and CA33000. Accordingly, the United States government has certain rights in the invention.

FIELD OF THE INVENTION

The present invention relates to novel peptides and methods of inhibiting tumor metastasis.

BACKGROUND OF THE INVENTION

Selectins are cell-surface carbohydrate binding proteins that mediate cell adhesion between leukocytes and the vascular endothelial surface. For example, binding of E-selectin to its ligand expressed on the surface of circulating neutrophils initiates rolling, and an early step in the recruitment of these cells to a site of injury or inflammation. Several potential therapeutics have been tested for their ability to inhibit adhesion of E-selectin to neutrophils, including carbohydrate-based molecules, antibodies, soluble E-selectin, and selectin-Ig chimeras. While these molecules have been useful to show the utility of selectin blockers for treating inflammation, each has significant shortcomings as a therapeutic, including short in vivo half-life, potential immunogenicity, high cost, and other side effects. A further drawback of these approaches is the lack of an efficient means to improve the pharmaceutical properties of these various molecules.

Cancer is a leading cause of death in developing countries. It is known that metastatic spread of cancer cells can not be prevented by surgery. Growing evidence suggests that carbohydrate-mediated cancer cell adhesion to selectins on the vascular endothelium is involved in the metastasis of a wide variety of epithelial cancers, including gastric, colorectal, pancreatic, liver, ovary, head and neck, and breast cancers. However, methods of effectively inhibiting carbohydrate-mediated cancer cell adhesion to selectins on the vascular endothelium are lacking.

Recent advances in methods for the preparation and screening of large numbers of individual peptides has led to the identification of numerous peptides useful in all areas of biomedical research, including research regarding the interaction of ligands to cell surface molecules. Even with these advances, however, compounds that effectively inhibit tumor metastasis are lacking. Thus, a need exists for compounds useful to treat cancer by inhibiting metastasis. This invention satisfies these needs and provides related advantages as well.

BRIEF DESCRIPTION OF THE INVENTION

In accordance with the present invention, there are provided peptides that bind to a member of the mammalian selectin family and inhibit the binding of a carbohydrate to said selectin. Invention peptides are useful to inhibit of the adhesion of cells containing particular cell-surface carbohydrates to cells containing cell-surface selectins.

Also provided in accordance with the present invention are pharmaceutical compositions comprising invention peptides useful in methods for inhibiting a carbohydrate from binding to a selectin, and in methods of inhibiting tumor cell metastasis and inflammation in a subject.

BRIEF DESCRIPTION OF THE FIGURES

FIG. 1A shows the binding of a cloned phage displaying IELLQAR (SEQ ID NO:7) peptide to various monoclonal anti-carbohydrate antibodies. FIG. 1B shows the binding of cloned phages to E-selectin. FIG. 1C shows the effect of IELLQAR (SEQ ID NO:7) and IDLLQAR phages on binding of sLe$^x$ to E-selectin; the control peptide is -FAQLDWH- (SEQ ID NO:38). FIG. 1D shows the effect of IELLQAR (SEQ ID NO:7) phage on binding of sLe$^x$ to E-, L- and P-selectins. FIG. 1E shows the effect of synthetic IELLQAR (SEQ ID NO:7) peptides on the binding between sLe$^x$ and E-selectin. Peptides used were linear IELLQAR (SEQ ID NO:7) (□), cyclic CIELLQARC (SEQ ID NO:13) (■) (the cysteins were linked by disulfide bonds), and IELLQAR (SEQ ID NO:7) multivalent (○) (Fmoc eight branch). FIG. 1F shows the effect of IELLQAR (SEQ ID NO:7) phage on the binding of HL-60 cells to E-selectin:IgG.

FIG. 2A shows the number of metastatic foci of mouse B16 melanoma formed in the lungs of mice pre-treated with control phage (left bar) or IELLQAR (SEQ ID NO:7) phage (right bar). FIG. 2B shows the number of metastatic foci of mouse B16 melanoma formed in lungs of mice pre-treated with control peptide (left bar) or IELLQAR (SEQ ID NO:7) peptide (right bar). FIG. 2C shows the number of metastatic foci of human MeWo melanoma formed in lungs of mice pre-treated with control peptide (left bar) or IELLQAR (SEQ ID NO:7) peptide (right bar).

DETAILED DESCRIPTION OF THE INVENTION

Figure 1:
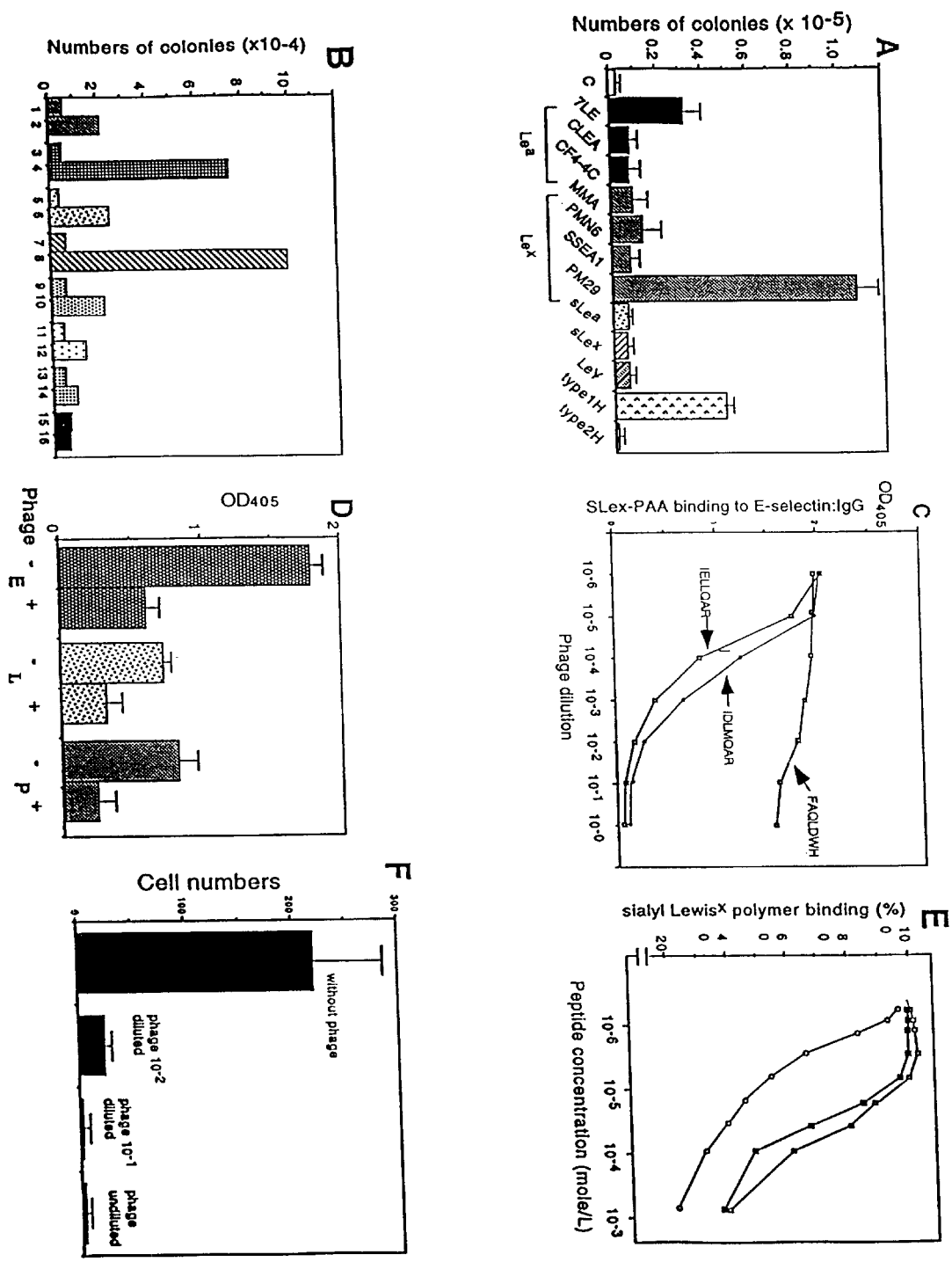
FIGS. 1A–1F shows results obtained in Example II.

In accordance with the present invention, there are provided peptides that bind to a member of the mammalian selectin family and inhibit the binding of a carbohydrate to the selectin. Invention peptides are further characterized by having the ability to functionally mimic naturally occurring carbohydrate ligands that bind to selectins on the surface of a cell. Invention peptides can therefore be referred to herein as "carbohydrate-mimicking."

As used herein the term "peptide" refers to compounds comprising two or more amino acids that are linked by peptide bonds. Invention peptides can be comprised in larger molecules, such as larger peptides, proteins, fragments of proteins, peptoids, peptidomimetics and the like. A peptide can be a non-naturally occurring molecule, which does not occur in nature, but is produced as a result of in vitro methods, or can be a naturally occurring molecule such as a protein or fragment thereof expressed from a cDNA library. Peptides can be either linear, cyclic or multivalent, and the like, which conformations can be achieved using methods well-known in the art.

As used herein, the term "amino acid" is used generally to include naturally occurring proteogenic amino acids as well as non-naturally occurring amino acids such as D-amino acids and amino acid analogs, any of which can be incorporated into a peptide using the methods otherwise known in the art. In view of this definition, one skilled in the art would know that reference herein to an amino acid, unless specifically indicated otherwise, includes, for example, naturally occurring proteogenic L-amino acids, D-amino acids, chemically modified amino acids such as amino acid analogs, naturally occurring non-proteogenic amino acids such as norleucine, and chemically synthesized compounds having properties known in the art to be characteristic of an amino acid. As used herein, the term "proteogenic" indicates that the amino acid can be incorporated into a protein in a cell through well known metabolic pathways.

As used herein, the phrase "a member of the mammalian selectin family" refers to the well-known cell-surface proteins that are able to bind to carbohydrates. Exemplary selectins include E-selectin (also known as LECAM-2, and ELAM-1), L-selectin (also known as LECAM-1, LAM-1 and gp90MEL), and P-selectin (also known as LECAM-3 and GMP-140) (see Bevilacqua et al, 1989, *Science*, 243:1160–1165; Johnston et al, 1989, *Cell*, 56:1033–1044; Laskey et al., 1989, *Cell*, 56:1045–1055; and Tedder et al., 1989, *J. Exp. Med.*, 170:123–133, and the like, each of which is incorporated herein by reference in their entirety). Each selectin has been found to recognize the oligosaccharide sialyl Lewis$^x$ (sLe$^x$), and E-selectin has been found to recognize both sLe$^x$ and sialyl Lewis$^a$ (sLe$^a$) (Berg et al., 1991, *J. Biol. Chem.* 266:14869; and Takada et al., 1991, *Biochem. Biophys. Res. Comm.* 179:713).

As used herein, the term "carbohydrate" refers to the well-known polyhydroxyl aldehydes or ketones. Carbohydrates exist as either mono-, oligo-, or poly-saccharides. Exemplary oligosaccharide carbohydrates include:
lacto-N-tetraosylceramide,
  Galβ1→3GlcNAcβ1→3Galβ1→4Glc-Cer; lacto-N-neotetraosylceramide,
  Galβ1→GlcNAcβ1→3Galβ1→4Glc-Cer;
sialyl Lewis$^x$, NeuNAcα2→3Galβ1→4(Fucα1→3)GlcNAcβ1→3Gal;
sialyl Lewis$^a$, NeuNAcα2→3Galβ1→3(Fucα1→4)GlcNAcβ1→3Gal;
Lewis$^x$, Galβ1→4(Fucα1→3)GlcNAcβ1→3Gal;
Lewis$^a$, Galβ1→3(Fucα1→4)GlcNAcβ1→3Gal;
Lewis$^y$, Fucα1→2Galβ1→4(Fucα1→3)GlcNAcβ1→3Gal;
type1H, Fucα1→2Galβ1→3GlcNAcβ1→3Gal; and
type2H, Fucα1→2Galβ1→4GlcNAcβ1→3Gal.

Selectins are cell-surface carbohydrate-binding proteins that have been found to mediate cell adhesion between leukocytes and the vascular endothelial surface. Although the primary function of selectins is to recruit leukocytes to vascular endothelial site, increasing evidence suggests an involvement of E-selectin in tumor metastasis for a variety of cancers (Irimura T., *Seminars Cancer Biol.*, 4:319 (1993); Miyaska M., *Clin. Orthop.* 312:10 (1995); McEver, R. P., *Glycoconjugate J.* 4:585 (1997); Kannagi, R., ibid 4:577 (1997); Takada et al, *Cancer Res.* 53:354 (1993); Sato et al., *Anticancer Res*, 17:3505 (1997); Martin-Satue et al., *Cancer Res.* 58:1544 (1998); Tozeren et al., *Int. J. Cancer*, 60:426 (1995); Nakashio et al., *Anticancer Res* 17:293 (1997); Wenzel et al., *Arch. Otolaryngol Head Neck Surg.* 121:1279 (1995); Sawada et al., *J. Biol. Chem.* 269:1425 (1994); Sawada et al., *J. Biol. Chem.* 268:12657 (1993). It is believed that the level of sialyl Lewis$^x$ (sLe$^x$) and/or sialyl Lewis$^a$ (sLe$^a$) carbohydrate antigens apparently increases during progression from non-metastatic to metastatic tumors. For example, colorectal carcinomas with poor clinical prognosis are characterized by high levels of sLe$^x$ or sLe$^a$ expression (see, e.g., Nakamori et al., 1993, *Cancer Res.*, 53:3632–3637; Irimura et al., 1993, *Cancer Biol.*, 4:319–324; and the like). Thus, compounds comprising invention peptides that inhibit the binding of sLe$^x$ and/or sLe$^a$ to E-selectin are contemplated herein for use to inhibit tumor metastasis.

As used herein the term "inhibit" or "inhibits" means the reduction or prevention of the particular activity being analyzed. For example, invention peptides described herein function to reduce or prevent the binding of carbohydrates to selectins. An invention peptide can inhibit the binding of carbohydrates displayed on cancerous cells from binding to cell-surface selecting, preferably E-selectin. Thus, inventions peptides are contemplated herein for use to inhibit cell:cell adhesion. The inhibition of sLe$^x$ and/or sLe$^a$, which are known to mediate tumor metastasis in various cancers, from binding to a cell-surface selectin is therefore useful in invention methods described herein to inhibit tumor cell metastasis in mammals, preferably humans. Preferably the invention peptide inhibits the binding of either one or both of sLe$^x$ or sLe$^a$ to a cell-surface selectin.

As used herein, the term "tumor" means a mass of transformed cells that are characterized, at least in part, by containing angiogenic vasculature. The term "tumor" is used broadly to include the tumor parenchymal cells as well as the supporting stroma, including the angiogenic blood vessels that infiltrate the tumor parenchymal cell mass. Although a tumor generally is a malignant tumor, i.e., a cancer having the ability to metastasize, a tumor also can be nonmalignant, provided that neovascularization is associated with the tumor. Tumor cells contemplated herein are derived from metastatic tumors. As used herein, the term "metastasis" refers to a secondary tumor that grows separately from the primary and has arisen from detached, transported cells.

The heptapeptides of the invention were identified by screening a combinatorial peptide library for peptides that bound to the anti-Lewis$^a$ monoclonal antibody (Mab) referred to as Mab clone 7LE (see, e.g., Example I). As disclosed herein, invention peptides having the general amino acid structural motif shown as SEQ ID NOS: 1–3, or having essentially the amino acid sequence shown as SEQ ID NOs:1–37 can effectively inhibit the binding of carbohydrates to selecting, preferably the binding of sLe$^a$ and sLe$^x$ to E-selectin. As used herein, the term "essentially the amino acid sequence" means a sequence having a single amino acid substitution as compared to the reference peptide. The skilled artisan will recognize that similar methods as disclosed in Example I can be used to identify additional peptides that effectively inhibit the binding of carbohydrates to lectins, preferably the binding of sLe$^a$ and sLe$^x$ to E-selectin.

Exemplary peptides for use herein comprise a heptapeptide amino acid sequence motif selected from the group consisting of:
  -IX$_1$LX$_2$QX$_3$R- (SEQ ID NO:1);
  -X$_1$X$_2$LLX$_3$AR- (SEQ ID NO:2); and
  -IX$_1$LLX$_2$X$_3$R- (SEQ ID No:33).

The amino acid "X" or "X$_n$" is used herein in its conventional form to refer to any one of the 20 naturally occurring amino acids, or non-natural modified forms thereof. In the heptapeptide motif corresponding to SEQ ID NO:1, amino acid X$_1$ is preferably S, D, F, I or E; X$_2$ is preferably L or M; and X$_3$ is preferably A, Q or G. In the heptapeptide motif corresponding to SEQ ID NO:2, amino acid X$_1$ is preferably I or F; X$_2$ is preferably S, D, F, I or E; and X$_3$ is preferably Q, W, G or D. In the heptapeptide motif corresponding to SEQ ID NO:33, amino acid X$_1$ is preferably S, D, F, I or E; X$_2$ is preferably Q, W, G or D; and X$_3$ is preferably A, Q or G. A particularly preferred heptapeptide within the motif corresponding to SEQ ID NO:2 is -FSLLDAR- (SEQ ID NO:12). A particularly preferred heptapeptide within the motif corresponding to SEQ ID NO:33 is -IFLLWQR- (SEQ ID NO:34).

Additional exemplary peptides for use herein comprise a heptapeptide amino acid sequence motif selected from the group consisting of:
  -IX$_1$LX$_2$QAR- (SEQ ID NO:3);
  -IX$_1$LLQX$_2$R- (SEQ ID NO:4); and
  -IX$_1$LLX$_2$AR- (SEQ ID NO:5).

In the heptapeptide motif corresponding to SEQ ID NO:3, amino acid $X_1$ is preferably S, D, F, I, or E; and $X_2$ is preferably L or M. In the heptapeptide motif corresponding to SEQ ID NO:4, amino acid $X_1$ is preferably S, D, I, F, or E; and $X_2$ is preferably A, Q or G. In the heptapeptide motif corresponding to SEQ ID NO:5, amino acid $X_1$ is preferably S, D, F I, or E; and $X_2$ is preferably Q, G, W or D.

Particularly preferred heptamers within the motif corresponding to SEQ ID NOs:3, 4 or 5 include of -IDLMQAR- (SEQ ID NO:9), -IILLQGR- (SEQ ID NO:10), and -ISLLGAR- (SEQ ID NO:11).

A particularly preferred exemplary group of peptides for use herein comprises a heptapeptide amino acid sequence motif corresponding to:

-IXLLQAR- (SEQ ID NO:6).

In the heptapeptide motif corresponding to SEQ ID NO:6, although amino acid X can be any amino acid, it is preferably S, D, F, I, or E. Particularly preferred heptapeptides within the motif corresponding to SEQ ID NO:6 include -IELLQAR- (SEQ ID NO:7), and -ISLLQAR- (SEQ ID NO:8).

The use of peptides as therapeutic agents is particularly advantageous because peptides can be synthesized in large numbers at relatively low cost and they can be readily modified to exhibit diverse properties (see, for example, Rees et al., *Protein Engineering: A Practical Approach* (IRL Press 1992), which is incorporated herein by reference). Carbohydrate mimicking invention peptides can be synthesized using a modification of the solid phase peptide synthesis method (Merrifield (*J. Am. Chem. Soc.*, 85:2149 (1964); Houghten, U.S. Pat. No. 4,631,211, issued Dec. 23, 1986, each of which is incorporated herein by reference) or can be synthesized using standard solution methods well known in the art (see, for example, Bodanszky, M., *Principles of Peptide Synthesis* 2nd ed. (Springer-Verlag, 1988 and 1993, suppl.), each of which is incorporated herein by reference). Peptides prepared by the method of Merrifield can be synthesized using an automated peptide synthesizer such as the Applied Biosystems 431A-01 Peptide Synthesizer (Mountain View, Calif.) or using a manual peptide synthesis method (Houghten, supra, 1986).

As disclosed herein, invention heptapeptides were identified by screening a combinatorial heptapeptide library (see Example I). In view of the disclosed methods, the skilled artisan would recognize that combinatorial libraries of peptides having more than seven amino acids or less than seven amino acids also can be screened to identify other peptides that inhibit carbohydrate binding to cell-surface lectins, preferably selectins. Furthermore, while the disclosed methods can be used to identify peptides that inhibit the binding of Lewis$^a$- and/or Lewis$^x$-mimicking peptides to selecting, the skilled artisan would know that similar methods can be used to optimize or to identify additional carbohydrate-mimicking peptides that inhibit the binding of these particular carbohydrates as well as other species of carbohydrates to various lectins.

For example, it is expected that those of skill in the art can use combinatorial synthetic analog technology coupled to rapid screening methods to optimize and identify additional invention peptides with increased binding affinity for E-selectin that possess enhanced therapeutic potential. Phage display technology provides a means for expressing a diverse population of random or selectively randomized peptides. Various methods of phage display and methods for producing diverse populations of peptides are well known in the art. For example, Ladner et al. (U.S. Pat. No. 5,223,409, issued Jun. 29, 1993, which is incorporated herein by reference) describe methods for preparing diverse populations of binding domains on the surface of a phage. In particular, Ladner et al. describe phage vectors useful for producing a phage display library, as well as methods for selecting potential binding domains and producing randomly or selectively mutated binding domains.

Accordingly, based on the heptapeptide peptide sequences disclosed in Table I, those of skill in the art would expect that smaller peptide sequences can be produced that would also bind cell-surface selecting. Thus, also contemplated herein are carbohydrate-mimicking, lectin-binding peptides comprising hexamer amino acid motifs set forth as:

-$X_1LLX_2X_3R$- (SEQ ID NO:36),
-$X_1LX_2QX_3R$- (SEQ ID NO:14),
-$X_1LX_2QAR$- (SEQ ID NO:15),
-$X_1LLX_2AR$- (SEQ ID NO:16), and
-$X_1LLQX_2R$- (SEQ ID NO:17).

In the hexapeptide motif corresponding to SEQ ID NO:36, amino acid $X_1$ is preferably S, D, F, I or E; $X_2$ is preferably Q, G, D or W; and $X_3$ is preferably A, Q or G. In the hexapeptide motif corresponding to SEQ ID NO:14, amino acid $X_1$ is preferably S, D, F, I or E; $X_2$ is preferably L or M; and $X_3$ is preferably A, Q or G. In the hexapeptide motif corresponding to SEQ ID NO:15, amino acid $X_1$ is preferably S, D, F, I or E; and $X_2$ is preferably L or M. In the hexapeptide motif corresponding to SEQ ID NO:16, amino acid $X_1$ is preferably S, D, F, I or E; and $X_2$ is preferably Q, G, D or W. In the hexapeptide motif corresponding to SEQ ID NO:17, amino acid $X_1$ is preferably S, D, F, I or E; and $X_2$ is preferably A, Q or G.

Preferred invention hexamer peptides comprise
-SLLQAR- (SEQ ID NO:18),
-DLMQAR- (SEQ ID NO:19),
-ILLQGR- (SEQ ID NO:20),
-SLLGAR- (SEQ ID NO:21),
-SLLDAR- (SEQ ID NO:22),
-ELLQAR- (SEQ ID NO:23),
-FLLWQR- (SEQ ID NO:37).

Invention pentamer peptides that bind to a selectin and inhibit carbohydrate binding are also contemplated herein, and include:

-LLX$_1$X$_2$R- (SEQ ID NO:35),
-LX$_1$QX$_2$R- (SEQ ID NO:24),
-LXQAR- (SEQ ID NO:25),
-LLXAR- (SEQ ID NO:26), and
-LLQXR- (SEQ ID NO:27).

In the pentapeptide motif corresponding to SEQ ID NO:35, amino acid $X_1$ is preferably Q, W, G or D; and $X_2$ is preferably A, Q or G. In the pentapeptide motif corresponding to SEQ ID NO:24, amino acid $X_1$ is preferably L or M; and $X_2$ is preferably A, Q or G. In the pentapeptide motif corresponding to SEQ ID NO:25, amino acid X is preferably L or M. In the pentapeptide motif corresponding to SEQ ID NO:26, amino acid X is preferably Q, W, G or D. In the pentapeptide motif corresponding to SEQ ID NO:27, amino acid X is preferably A, Q or G.

Preferred invention pentamer peptides include:
-LLQAR- (SEQ ID NO:28), -LMQAR- (SEQ ID NO:29), -LLGAR-(SEQ ID NO:30), -LLDAR- (SEQ ID NO:31), and -LLQGR- (SEQ ID NO:32).

The invention carbohydrate-mimicking peptides can be synthesized using L-amino acids, the active groups of which are protected as required using, for example, a t-butyldicarbonate (t-BOC) group or a fluorenylmethoxy carbonyl (FMOC) group. Amino acids and amino acid analogs can be purchased commercially (Sigma Chemical Co., St. Louis Mo.; Advanced Chemtec, Louisville Ky.) or synthesized using methods known in the art. Peptides synthesized using the solid phase method can be attached to a variety of resins, including, for example, 4-methylbenzhydrylamine (MBHA), 4-(oxymethyl)-phenylacetamido methyl and 4-(hydroxymethyl) phenoxymethyl-copoly(styrene-1% divinylbenzene (Wang resin), all of which are commercially available, or to p-nitrobenzophenone oxime polymer (oxime resin), which can be synthesized as described by De Grado and Kaiser, *J. Org. Chem.* 47:3258 (1982), which is incorporated herein by reference.

The choice of amino acids or amino acid analogs incorporated into an invention peptide will depend, in part, on the specific physical, chemical or biological characteristics required of the carbohydrate-mimicking, lectin-binding peptide. Such characteristics are determined by whether, for example, the peptide is to be used in vivo or in vitro, and, when used in vivo, by the route by which the invention peptide will be administered or the location in a subject to which it will be directed. For example, the carbohydrate-mimicking, lectin-binding peptides exemplified herein can be synthesized using only L-amino acids. However, the skilled artisan would know that any or all of the amino acids in a peptide of the invention can be a naturally occurring L-amino acid, a non-naturally occurring D-amino acid or an amino acid analog, provided the peptide can reduce or inhibit binding of a carbohydrate to a lectin.

The choice of including an L-amino acid or a D-amino acid in the invention peptides depends, in part, on the desired characteristics of the peptide. For example, the incorporation of one or more D-amino acids can confer increased stability on the peptide in vitro or in vivo. The incorporation of one or more D-amino acids also can increase or decrease the activity, such as selectin binding affinity, of the peptide as determined, for example, using the assay described herein in Example IIB or other well known methods for determining the binding affinity of a particular peptide to a particular protein.

As set forth above, invention peptides can be either linear, cyclic or multivalent, and the like, which conformations can be achieved using methods well-known in the art. As used herein a "cyclic" peptide refers to analogs of synthetic linear peptides that can be made by chemically converting the structures to cyclic forms. Cyclization of linear peptides can modulate bioactivity by increasing or decreasing the potency of binding to the target protein (Pelton, J. T., et al., *Proc. Natl. Acad. Sci., U.S.A.,* 82:236–239). Linear peptides are very flexible and tend to adopt many different conformations in solution. Cyclization acts to constrain the number of available conformations, and thus, favor the more active or inactive structures of the peptide. The immunogenicity of synthetic peptides has been correlated with the experimentally observed conformational preferences in solution (Dyson, H., et al., 1988, *Annual Review of Biophysics and Biophysical Chemistry,* 17:305–324). Differences in immunogenicity may be indicative of differences in binding affinity of specific antibodies for cyclic peptides.

Cyclization of linear peptides is accomplished either by forming a peptide bond between the free N-terminal and C-terminal ends (homodetic cyclopeptides) or by forming a new covalent bond between amino acid backbone and/or side chain groups located near the N- or C-terminal ends (heterodetic cyclopeptides) (Bodanszky, N., 1984, supra). The latter cyclizations use alternate chemical strategies to form covalent bonds, e.g. disulfides, lactones, ethers, or thioethers. Linear peptides of five or more amino acid residues, as described herein, can be cyclized relatively easily. The propensity of the peptide to form a beta-turn conformation in the central four residues facilitates the formation of both homo- and heterodetic cyclopeptides. The presence of proline or glycine residues at the N- or C-terminal ends also facilitates the formation of cyclopeptides, especially from linear peptides shorter than six residues in length.

As used herein, the term "multivalent" peptides refers to more than one particular peptide per molecule. The peptides, preferably synthetic, can be either the same or different. Exemplary multivalent peptides can be produced using the well-known multiple antigen peptide system (MAPS; see, e.g., Briand et al., 1992, *J. Immunol Meth.,* 156(2):255–265; Schott et al., 1996, *Cell Immun.,* 174(2):199–209, and the like).

In some cases, it can be desirable to allow an invention peptide to remain active for only a short period of time. In those cases, the incorporation of one or more L-amino acids in the peptide can allow, for example, endogenous peptidases in a subject to digest the peptide in vivo, thereby limiting the subject's exposure to the invention carbohydrate-mimicking, lectin-binding, metastasis-inhibiting peptide. The skilled artisan can determine the desirable characteristics required of an invention peptide by taking into consideration, for example, the age and general health of a subject, and the like. The half life in a subject of a peptide having, for example, one or more D-amino acids substituted for a corresponding L-amino acid can be determined using methods well known to those in the field of pharmacology.

Selective modification of the reactive groups in a peptide also can impart desirable characteristics to a carbohydrate-mimicking, lectin-binding invention peptide. An invention peptide can be manipulated while still attached to the resin to obtain, for example, an N-terminal modified peptide such as an N-acetylated peptide. Alternatively, the peptide can be removed from the resin using hydrogen fluoride or an equivalent cleaving reagent and then modified. Compounds synthesized containing the C-terminal carboxy group (Wang resin) can be modified after cleavage from the resin or, in some cases, prior to solution phase synthesis. Methods for modifying the N-terminus or C-terminus of a peptide are well known in the art and include, for example, methods for acetylation of the N-terminus and methods for amidation of the C-terminus.

Also encompassed within the scope of invention peptides are peptide analogs. As used herein, the term "peptide analog" includes any peptide having an amino acid sequence substantially the same as a sequence specifically shown herein, such as SEQ ID NOs:1–37, in which one or more residues have been conservatively substituted with a functionally similar residue and which displays the ability to functionally mimic an invention lectin-binding peptide as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

As used herein the phrase "conservative substitution" also includes the use of a chemically derivatized residue in place of a non-derivatized residue, provided that such peptide displays the required lectin binding activity. The phrase "chemical derivative" refers to a subject peptide having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Peptides of the present invention also include any peptide having one or more additions and/or deletions of residues, relative to the sequence of a peptide whose sequence is shown herein, so long as the required activity is maintained.

The amino acid length of molecules comprising invention peptides and analogs thereof, can range from about 5 amino acids up to a full-length protein sequence depending on which invention peptide is being employed. In certain embodiments, the amino acid lengths of molecules comprising invention peptides include, for example, no more than about 5, no more than about 6, no more than about 7, no more than about 8, no more than about 9, no more than about 10, no more than about 20, no more than about 30, no more than about 40, no more than about 50, no more than about 75, no more than about 100, no more than about 150, no more than about 200, no more than about 250 or more amino acids in length up to a full-length protein sequence, wherein said protein is either native or chimeric.

In accordance with another embodiment of the invention, there are provided invention peptide/moiety conjugates comprising invention peptide, e.g., SEQ ID Nos:1–37 and the like, linked to a moiety. Because invention peptides and metastatic tumor cells both bind to cell-surface selecting, an invention peptide can be used, for example, to target a moiety to a tumor, or to the proximity of a tumor, by linking the moiety to the invention peptide to produce an invention peptide/moiety conjugate and administering the conjugate to a subject having a tumor. As used herein, the term "moiety" is used broadly to mean a physical, chemical, or biological material that is linked to an invention peptide for the purpose of being targeted in vivo to a tumor or to angiogenic vasculature expressing a selectin, preferably E-selectin recognized by the invention peptide. In particular, a moiety is a biologically useful moiety such as therapeutic moiety, a diagnostic moiety or a drug delivery vehicle. Thus, a moiety can be a therapeutic agent, for example, a cancer chemotherapeutic agent such as doxorubicin, which, when linked to an invention peptide, provides a conjugate useful for treating a cancer in a subject. In addition, a moiety can be a drug delivery vehicle such as a chambered microdevice, a cell, a liposome or a virus, which can contain an agent such as a drug or a nucleic acid.

As used herein, the "targeting" in reference to targeting a moiety to a tumor, refers to the invention peptide portion of the conjugate either attaching directly to the tumor, or attaching to a cell-surface selectin on a selectin-expressing cell, such as a vascular endothelial cell, in close proximity to the tumor. When the invention conjugate attaches to a selectin-expressing vascular endothelial cell, it preferably attaches in close enough proximity to the tumor such that the moiety conjugated to the invention peptide comes in contact with the tumor.

A moiety also can be a molecule such as a polypeptide or nucleic acid, to which an invention peptide is grafted for the purpose of directing the polypeptide or nucleic acid to a selected tumor (Smith et al., *J. Biol. Chem.* 269:32788–32795 (1994); Goldman et al., *Cancer Res.* 15:1447–1451 (1997), each of which is incorporated herein by reference). For example, an invention peptide can be expressed as a fusion protein with a desired polypeptide such that the peptide targets the grafted polypeptide to a selected tumor. Such a desired polypeptide, which is grafted to the invention peptide, can be a polypeptide involved in initiating a cell death pathway, for example, caspase 8, thus providing a means to direct caspase 8 to a tumor, where it can induce apoptosis of the tumor cells or of the vasculature supplying the tumor. An invention peptide also can be grafted to a polypeptide expressed by a virus, for example, the adenovirus penton base coat protein, thus providing a means to target a virus to a tumor (Wickham et al., *Gene Ther.* 2:750–756 (1995); Weitzman et al., In: "Gene Therapy and Vector Systems" 2:17–25 (1997), each of which is incorporated herein by reference). Such a grafted virus can contain an exogenous gene useful in a method of gene therapy. Accordingly, the invention provides compositions of matter comprising an invention peptide/moiety conjugate.

A moiety can be a detectable label such a radiolabel or can be a cytotoxic agent, including a toxin such as ricin or a drug such as a chemotherapeutic agent or can be a physical, chemical or biological material such as a liposome, microcapsule, micropump or other chambered microdevice, which can be used, for example, as a drug delivery system. Generally, such microdevices, should be nontoxic and, if desired, biodegradable. Various moieties, including microcapsules, which can contain an agent, and methods for linking a moiety, including a chambered microdevice, to a molecule of the invention are well known in the art and commercially available (see, for example, "Remington's Pharmaceutical Sciences" 18th ed. (Mack Publishing Co. 1990), chapters 89–91; Harlow and Lane, *Antibodies: A laboratory manual* (Cold Spring Harbor Laboratory Press 1988), each of which is incorporated herein by reference; see, also, Hermanson, supra, 1996).

The skilled artisan will recognize that various other chemotherapeutic agents also can be linked to an invention peptide to make a conjugate of the invention. Cancer chemotherapeutic agents have been linked to antibodies, for example, for the purpose of targeting the agents to cells such as tumor cells that express the antigen recognized by the antibodies. In addition, in such antibody/drug conjugates, the agent can maintain its therapeutic function and the antibody can maintain its antigen binding specificity. For example, the anthracyclin, doxorubicin, has been linked to antibodies and the antibody/doxorubicin conjugates have been therapeutically effective in treating tumors (Sivam et al., *Cancer Res.* 55:2352–2356 (1995); Lau et al., *Bioorg. Med. Chem.* 3:1299–1304 (1995); Shih et al., *Cancer Immunol. Immunother.* 38:92–98 (1994)). Analogous to antibody-based conjugates, other anthracyclins, including idarubicin and daunorubicin, can be chemically conjugated to invention peptides to deliver effective doses of the agents to tumors (Rowland et al., *Cancer Immunol. Immunother.*

37:195–202 (1993); Aboud-Pirak et al., *Biochem. Pharmacol.* 38:641–648 (1989)).

In addition to the anthracyclins, alkylating agents such as melphalan and chlorambucil can be linked to invention peptides to produce therapeutically effective conjugates (Rowland et al., supra, 1994; Smyth et al., *Immunol. Cell Biol.* 65:315–321 (1987)), as can vinca alkaloids such as vindesine and vinblastine (Aboud-Pirak et al., supra, 1989; Starling et al., *Bioconj. Chem.* 3:315–322 (1992)). Analogous to antibody-based conjugates, conjugates of invention peptides and antimetabolites such as 5-fluorouracil, 5-fluorouridine and derivatives thereof can be effective in treating tumors (Krauer et al., *Cancer Res.* 52:132–137 (1992); Henn et al., *J. Med. Chem.* 36:1570–1579 (1993)). Other chemotherapeutic agents, including cis-platinum (Schechter et al., *Int. J. Cancer* 48:167–172 (1991)), methotrexate (Shawler et al., *J. Biol. Resp. Mod.* 7:608–618 (1988); Fitzpatrick and Garnett, *Anticancer Drug Des.* 10:11–24 (1995)) and mitomycin-C (Dillman et al., *Mol. Biother.* 1:250–255 (1989)) also are therapeutically effective when administered as conjugates with various different invention peptides.

Since the moiety component of an invention peptide/moiety conjugate can comprise a substantial portion of the conjugate without adversely affecting the ability of the invention peptide to bind a selectin in close proximity to a tumor, additional components can be included as part of the conjugate, if desired. For example, in some cases, it can be desirable to utilize an oligopeptide spacer between an invention peptide and the moiety (Fitzpatrick and Garnett, *Anticancer Drug Des.* 10:1–9 (1995)). In this way, panels of moiety/spacer complexes can be constructed, in which a common spacer is linked to various different moieties. Such panels of moiety/spacer conjugates can facilitate linkage of the moiety to an invention peptide.

In accordance with another embodiment of the present invention, there are provided pharmaceutical compositions comprising any of the invention peptides or analogs thereof described herein, alone or in various combinations with each other. Invention pharmaceutical compositions preferably further comprise an acceptable carrier. Thus, the invention provides pharmaceutical compositions comprising an invention peptide and a pharmaceutically acceptable carrier.

The carbohydrate-mimicking, lectin-binding peptide compositions described herein can be used, for example, in methods for inhibiting the binding of carbohydrates to lectins, preferably for inhibiting the binding of oligosaccharides to selecting, and the like. Invention peptides are particularly useful for inhibiting the binding of sLe$^a$ and sLe$^x$ to E-selectin, resulting in the inhibition of tumor metastasis. Thus, in accordance with another embodiment of the invention, there are provided methods for inhibiting tumor cell metastasis in a subject comprising administering an effective amount of an invention lectin-binding, preferably E-selectin binding, peptide to the subject. Exemplary lectin-binding peptides include SEQ ID Nos:1–37 described herein, and the like.

The invention methods described herein are contemplated for use to prevent or reduce the incidence of tumor metastasis for all forms of cancer. Exemplary forms of cancer contemplated herein for treatment include head and neck squamous cell carcinoma, colon carcinoma, lung adenocarcinoma, human gastric cancer, breast cancer, pancreatic cancer, liver cancer, ovarian cancer, leukemia, and the like.

In accordance with yet another embodiment of the invention, there are provided methods for inhibiting inflammation in a subject comprising administering an effective amount of an invention lectin-binding, preferably E-selectin binding, peptide to the subject. Exemplary lectin-binding peptides include SEQ ID Nos:1–37 described herein, and the like. The invention methods of inhibiting inflammation are useful for treating a variety of conditions, diseases or pathologies, in which reduction or prevention of inflammation is desired. For example, invention methods of inhibiting inflammation are useful for treating inflammation-associated pathologies that are caused, in whole or part, by inflammation or otherwise exhibit inflammation. Exemplary inflammation-associated pathologies or conditions include acute respiratory syndrome, ischemic perfusion, ulcerative inflammation, e.g., ulcerative cholitis, and the like, hyperplastic inflammation, cirrhotic inflammation, atrophic inflammation, and the like.

As used herein, the term "inflammation" refers to the well-known localized protective response elicited by injury or destruction of tissues, which serves to destroy, dilute, or wall off both the injurious agent and the injured tissue. Histologically, inflammation is characterized by a series of events including the migration of leukocytes into the inflammatory focus.

Pharmaceutically acceptable carriers are well known in the art and encompass any of the standard pharmaceutical carriers, including aqueous solutions such as physiologically buffered saline, water and emulsions such as an oil/water or water/oil emulsion, and various types of wetting agents, or other solvents or vehicles such as glycols, glycerol, vegetables oils (eg., olive oil) or injectable organic esters. A pharmaceutically acceptable carrier can be used to administer an invention peptide to a subject. A pharmaceutically acceptable carrier also can be useful for contacting an invention peptide with a cell in vitro.

A pharmaceutically acceptable carrier can contain physiologically acceptable compounds that act, for example, to stabilize the invention peptide or increase or decrease the absorption of the agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and sorbic acid.

The choice of a pharmaceutically acceptable carrier, including a physiologically acceptable compound, depends, for example, on the route of administration of the invention peptide and on the particular physico-chemical characteristics of the specific invention peptide. For example, a physiologically acceptable compound such as aluminum monosterate or gelatin is particularly useful as a delaying agent, which prolongs the rate of absorption of a pharmaceutical composition administered to a subject by injection.

The determination that the carbohydrate-binding activity of a lectin is reduced or inhibited can be made, for example, using the assays disclosed in the Examples herein. The skilled artisan would know other routine methods for determining whether tumor cell metastasis has been reduced or inhibited in vitro or in vivo due to administration of a invention peptide.

A pharmaceutical composition containing an invention peptide can be administered to a subject by various routes, including orally, parenterally, intravenously, intramuscularly, subcutaneously, intraorbitally, intracapsularly, intraperitoneally, intracisternally, intravaginally, rectally or by passive or facilitated absorption through the skin using, for example, a skin patch or transdermal iontophoresis, respectively. The composition can be administered by bolus injection in a single dose, by multiple fractionated doses over a period of days or weeks or by continuous infusion. In addition, the composition can be administered over a sustained period of time, for example, using a dermal patch or an implant device such as a subdermal pump.

The pharmaceutical composition also can be incorporated, if desired, into liposomes, microspheres or other polymer matrices (see, for example, Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer.

As shown in the Examples, an effective amount of various invention peptides inhibited transformed cancerous cells from binding to E-selectin in vitro (see, also, Example II) and inhibited human transformed cancerous cells from metastasizing in vivo. In view of the results disclosed herein, the skilled artisan would recognize that an effective amount of a particular invention peptide can vary depending on several factors, including the activity of the invention peptide, other components, if any, present in a pharmacologically acceptable composition containing the peptide, and the physico-chemical properties of the peptide as discussed previously. The concentration of an invention peptide that is useful as an effective amount based on the methods described herein (see Example II) or otherwise well known in the art.

In accordance with the present invention, an "effective amount" of an invention peptide can inhibit a carbohydrate, such as sLe$^a$ and/or sLe$^x$, from binding to a selectin, preferably E-selectin. The invention methods are as preferably used to inhibit sLe$^a$ and/or sLe$^x$, from binding to E-selectin in a subject. As used herein, a "subject" means a mammal, including, for example, a human, a monkey or a cat, and the like. An effective amount of an invention peptide is preferably within the range of about 0.01 to about 100 mg/kg body weight, and can be readily determined by considering the activity of the particular invention peptide being administered, the route of administration, the period over which the invention peptide is to be administered, and other factors known to those skilled in the art. Thus, the invention peptides described herein can be used as medicaments for the treatment of a variety of cancer pathologies by inhibiting tumor cell metastasis.

All U.S. patents and all publications mentioned herein are incorporated in their entirety by reference thereto. The invention will now be described in greater detail by reference to the following non-limiting examples.

Materials and Methods

Unless otherwise stated, the present invention was performed using standard procedures, as described, for example in Maniatis et al., *Molecular Cloning: A Laboratory Manual*, Cold Spring Harbor Laboratory Press, Cold Spring Harbor, N.Y., USA (1982); Sambrook et al., *Molecular Cloning: A Laboratory Manual* (2 ed.), Cold Spring Harbor Laboratory Press, Cold Spring Harbor, N.Y., USA (1989); Davis et al., *Basic Methods in Molecular Biology*, Elsevier Science Publishing, Inc., New York, USA (1986); or *Methods in Enzymology: Guide to Molecular Cloning Techniques* Vol.152, S. L. Berger and A. R. Kimmerl Eds., Academic Press Inc., San Diego, USA (1987)).

Monoclonal antibodies employed herein include: anti-Lewis$^x$: clone MMA, S. N. Hanjan, J. F. Kearney, M. D. Cooper. Clin. Immunol. Immunopath., 23, 172 (1982); clone SSEA-1, H. C. Gooi et al., Nature, 292, 156 (1981); clone PMN6, PMN29, J. L. Magnani, et al., Arch. Biochem. Biophys., 233, 501 (1984); anti-Lewis$^a$: clone 7LE, A. Takada et al., Cancer Res. 53, 354 (1993); clone CF4-4C, W. W. Young Jr. et al., J. Biol. Chem., 258, 4890 (1983); anti-sialyl Lewis$^x$: K. Fukushima et al., Cancer Res., 44, 5279 (1984); anti-sialyl Lewis$^a$, clone CA19-9, H. Koplowski et al., Science 212, 53 (1981); anti-Lewis$^y$: clone F3, K. O. Lloyd et al., Immunogenetics, 17, 537 (1983); anti-type 1H: clone101, P. Fredman et al., J. Biol. Chem., 258, 11206 (1983); anti type 2H: cloneBE-2, W. W. Young Jr, J., Portoukalian, S. Hackamore, J. Biol. Chem. 256, 10967 (1981).

EXAMPLE I

Identification of Peptides that Mimic Carbohydrate-mediated Antigens

In order to identify sLe$^a$-mimicking peptides, a phage-display library displaying linear heptapeptides was screened using an anti-carbohydrate, anti-Lewis$^a$ monoclonal antibody (clone 7LE, mouse IgG1, Seikagaku, Ijamsville, Md.). The selection of the antibody binding phage was carried out using well-known in vitro panning methods.

A flat bottom Linbro/Titertek 96 well plate (ICN Biomedicals, Aurora, Ohio) was coated with 10 mg purified goat anti-mouse immunoglobulin at 4° C. for 20 hours. Wells were blocked with PBS containing 3% BSA and 0.02% Tween 20 for 1 hour, then incubated with 2–3 mg monoclonal anti-Lewis$^a$ antibody at room temperature for 1 hour. After washing with PBS containing 0.02% Tween-20, wells were blocked with PBS containing 3% BSA. A linear heptapeptide phage library ($10^{11-12}$ transducing units) was added to the well and incubated at room temperature for 1 hour. Unbound phage was removed by washing with PBS containing 0.02% Tween-20. Competent K91 Kan bacteria were added and incubated at room temperature for 1 hour. Infected bacteria were then diluted in 20 ml LB, and an aliquot of the bacteria was plated on LB agar plates containing 100 mg/ml kanamycin and 20 mg/ml tetracycline. Plates were incubated at 37° C. overnight to allow bacteria to form colonies. The rest of the diluted bacteria was cultured in LB overnight at 37° C.

For the second screen, phage was recovered from the liquid overnight culture by precipitating with 6% polyethyleneglycol and 0.32M NaCl. Pelleted phage was dissolved in 1 ml PBS and used for screening with antibodies in the same manner as the first screen. After a third screen, individual colonies were subjected to DNA sequencing analysis using an ABI/PRISM dye terminater cycle kit (Parkin Elmer, Foster City, Calif.) to determine the respective amino acid structure of the peptide monoclonal antibody, which peptide sequences are set forth in Table 1.

TABLE I

Peptide sequences of phage clones isolated by
an anti-Lewis[a] monoclonal antibody clone 7LE.

| Peptide sequence | | |
|---|---|---|
| I<u>SLLQA</u>R | (9) | (SEQ ID NO: 8) |
| I<u>DLMQA</u>R | (4) | (SEQ ID NO: 9) |
| I<u>ILLQG</u>R | (2) | (SEQ ID NO: 10) |
| I<u>SLLGA</u>R | (2) | (SEQ ID NO: 11) |
| F<u>SLLDA</u>R | (2) | (SEQ ID NO: 12) |
| I<u>FLLQA</u>R | (1) | (SEQ ID NO: 7) |
| I<u>FLLWQ</u>R | (1) | (SEQ ID NO: 33) |

Among 26 clones sequenced, 21 had the consensus sequence shown here. Common amino acid residues (15) are underlined. The number of clones encoding the same peptide is shown in parentheses.

As evidenced by Table 1, this screening yielded several phage clones containing peptides with the following consensus sequence for binding the anti-Lewis[a] monoclonal antibody used as a target:

-IX$_1$LX$_2$QX$_3$R- (SEQ ID NO:1);
-X$_1$X$_2$LLX$_3$AR- (SEQ ID NO:2); and
-IX$_1$LLX$_2$X$_3$R- (SEQ ID NO:33).

EXAMPLE II

Reactivity of Cloned Phage and Synthetic Petides to Monoclonal Anti-carbohydrate Antibodies and Selectins A. Binding of a Cloned Phage Displaying IELLQAR (SEQ ID NO:7) Peptide to Various Monoclonal Anti-carbohydrate Antibodies The binding of the cloned phage containing the heptapeptide IELLQAR (SEQ ID NO:7), and the other peptides shown in Table 1, to various monoclonal anti-carbohydrate antibodies was analyzed by coating microtiter wells with various monoclonal antibodies corresponding to Mabs: 7LE, CLEA, CF4-4C, MMA, PMN6, SSEA1, PM29, sLe[a], sLe[x], Le[y], Type 1H, and Type 2H. Next, the IELLQAR (SEQ ID NO:7) peptide displaying phage was added to each well at a concentration of 1×10$^6$ transducing units. After incubating the phage for 1 hour, wells were washed and bound phage was recovered after transformation of competent K91 Kan bacteria in the same manner as described in Example I. Bacteria were plated on LB agar containing 20 mg/ml tetracycline and numbers of colonies appearing on plates were counted.

The results for heptapeptide IELLQAR (SEQ ID NO:7) are shown in FIG. 1A, and indicate that in addition to binding to binding to the anti-Lewis[a] Mab "7LE", the IELLQAR peptide also binds to anti-Lewis[x] (clone PMN29) antibody and anti-type1H (clone 101) antibody. Similar results were obtained for the other peptides listed in Table 1. The results therefore indicate that the peptides set forth in Table 1 did not show a general consensus for Lewis[a] antigen in that phage did not bind to other known anti-Lewis[a] antibodies, such as CLEA and CF4-4C (FIG. 1A). The results also indicated that sequences of the phage clones set forth in Table 1 crossreacted with the following antibodies with related carbohydrate epitopes: anti-Lewis[x] (clone PMN29) antibody and anti-type1H (clone 101) antibody (FIG. 1A). Thus, the peptides identified herein crossreact with both anti-Le[x] and anti-Le[a] antibodies, as well as anti-type 1H antibody.

B. Assay of Reactivity of Cloned Phage to E-selectin

Whether the peptides contained in the phage identified above (Table 1) react with E-selectin was assayed. A soluble form E-selectin was prepared as described in R. Sawada, S. Tsuboi, M. Fukuda, J. Biol. Chem., 269, 1425 (1994); R. Sawada, J. B. Lowe, M. Fukuda, J. Biol. Chem. 268, 12657 (1993); Sueyoshi, S. et al., J. Biol. Chem. 269, 32342 (1994). COS-1 cells were transfected with a mammalian expression plasmid vector encoding each respective selectin:IgG chimera using Lipofectamine+plus (Gibco BRL, Gaitherburg, Md.). Two days after transfection, culture supernatants were collected and selectin:IgG chimeras were purified by affinity chromatography on protein A. Microtiter wells were coated with E-, L-, or P-selectin:IgG chimeras (10 mg/ml) at 4° C. overnight, then blocked with TBS containing 1 mM CaCl$_2$ and 3% BSA for 2 hours. Phage (1×10$^6$ transducing units) was added to wells and incubated at room temperature for 1 hour. The control phage used in this experiment lacks a consensus heptapeptide. After washing wells with TBS containing 1 mM CaCl$_2$, bound phage was quantitated by transforming K91 Kan bacteria, followed by colony counting as described above.

The results are shown in the bar graph in FIG. 1B where the odd numbered bars in the graph are experiments conducted in the absence of calcium and the even numbered bars in the graph are experiments conducted in the presence of calcium. In the bar graph in FIG. 1B, bars 1,2 correspond to SEQ ID NO:8; bars 3,4 correspond to SEQ ID NO:9; bars 5,6 correspond to SEQ ID NO:10; bars 7,8 correspond to SEQ ID NO:7; bars 9,10 correspond to SEQ ID NO:11; and bars 11,12 correspond to SEQ ID NO:12; bars 13,14 correspond to SEQ ID NO:33; bars 15,16 correspond to the control peptide -FAQLDWH- (SEQ ID NO:38).

The results indicate, that all phage clones with the consensus sequences IXLXQXR (SEQ ID NO:1), -XXLLXAR- (SEQ ID NO:2), and -IXLLXXR- (SEQ ID NO:33) (Table 1) bound to E-selectin in a calcium dependent manner (FIG. 1B). The binding assay indicates that phage displaying the IELLQAR (SEQ ID NO:7) peptide sequence have the highest binding affinity for E-selectin, and phage displaying IDLMQAR (SEQ ID NO:9) have the second strongest binding affinity for E-selectin (FIG. 1B).

C. Effect of Consensus Sequence Bearing Phage and Peptides on Binding of sLe[x] to Selecting The inhibition of binding between sLe[x] and E-selectin:IgG by phage or peptides was assayed by adding five hundred ng of polymeric sLe[x] (sLe[x]-PAA-biotin, GlycoTech, Rocksville, Md.) to wells in the presence or absence of phage or peptide. After incubating at room temperature for 1 hour, wells were washed with TBS containing CaCl$_2$, and sLe[x]-PAA-biotin bound to each selectin was determined using the peroxidase conjugated avidin and peroxidase substrate ABTS (Pierce, Rockford, Ill.). The OD405 was read in an ELISA reader. The synthetic peptides used were linear IELLQAR (SEQ ID NO:7), cyclic <u>C</u>IELLQAR<u>C</u> (SEQ ID NO:13) (cysteins linked by disulfide bonds are underlined), and IELLQAR (SEQ ID NO:7) multivalent (Fmoc eight branch), which was synthesized by AnaSpec, Inc. (San Jose, Calif.).

To examine whether IELLQAR (SEQ ID NO:7) and IDLMQAR (SEQ ID NO:9) phage bind to E-selectin at the ligand binding site, competition between carbohydrate sLe[x] and these phage was examined as set forth above. The results shown in FIG. 1C indicate that both phage inhibited binding of sLe[x] to E-selectin, while the control phage lacking a consensus heptapeptide sequence did not show inhibitory activity. The inhibition assays indicated that a phage clone displaying IELLQAR (SEQ ID NO:7) peptide has the highest binding affinity for E-selectin among the isolated clones.

Because sLe[x] also binds to P-selectin and L-selectin, the effect of IELLQAR (SEQ ID NO:7) phage on the binding between sLe$^x$ and P- and L-selectins was assayed. The results shown in FIG. 1D indicate that IELLQAR (SEQ ID NO:7) phage inhibits binding between sLe$^x$ and both P- and L-selectins, though the binding affinities of this peptide toward P- and L-selectins are weaker than toward E-selectin.

Synthetic IELLQAR (SEQ ID NO:7) peptides were then tested for their reactivities to E-selectin (FIG. 1E). The linear heptapeptide inhibited binding between sLe$^x$ and E-selectin with a half inhibition value (IC$_{50}$) of $2 \times 10^{-4}$ M. The IC50 values for cyclic heptapeptide and for multivalent (8 branch MAPS) peptide were $1 \times 10^{-4}$ M and $1 \times 10^{-5}$ M, respectively. The IC50 for oligosaccharide sLe$^x$ reported in the literature ranges from $1 \times 10^{-4}$ M to $3 \times 10^{-3}$ M, depending on the methods employed (see, e.g., references in G. Weitz-Schmidt et al., Anal. Biochem., 238, 184 (1996); M. R. Nelson, et al., J. Clin. Invest. 91, 1157 (1993); J. K. Welpy et al., Glycobiology 4, 259 (1994); M. Anostario, S. H. Li, K. S. Huang, Anal. Biochem., 221, 317 (1994)). The binding affinity values of the heptapeptides obtained in this study should be comparable to an IC50 of $5.5 \times 10^{-4}$ M for sLe$^x$ oligosaccharide obtained by an ELISA binding assay using biotinylated sLe$^a$-PAA and E-selectin:IgG. It has also been found that these peptides also inhibited the binding between sLe$^a$ and E-selectin, suggesting that the heptapeptide IELLQAR (SEQ ID NO:7) binds to E-selectin at points common to both sLe$^x$ and sLe$^a$.

D. Effect of IELLQAR (SEQ ID NO:7) Phage on the Binding Between HL-60 Cells and E-selectin:IgG The effect of IELLQAR (SEQ ID NO:7) phage on the binding of sLe$^x$ expressing HL-60 cells to E-selectin was assayed using a cell binding assay as described in R. Sawada, S. Tsuboi, M. Fukuda, J. Biol. Chem., 269, 1425 (1994); R. Sawada, J. B. Lowe, M. Fukuda, J. Biol. Chem. 268, 12657 (1993). It has been found that cells expressing sLe$^x$ or sLe$^a$, including HL-60 cells, bind to E-selectin. Briefly, microtiter wells were coated with purified E-selectin:IgG chimera. After blocking with TBS containing 1 mM CaCl$_2$ and 3% BSA for 1 hour, wells were preincubated with the same buffer with or without inhibitor (phage or peptide) for 20 minutes. Human myelocytic leukemia HL-60 cells ($1 \times 10^4$ cells/well) were added and left at 4° C. for 1 hour. Unbound cells were then removed by washing the wells with TBS containing 1 mM CaCl$_2$. Numbers of HL-60 cells remained at the bottom of well were counted under a microscope. The results shown in FIG. 1F indicate that the phage inhibited the binding between HL-60 cells and E-selectin.

EXAMPLE III

In Vivo Assay of the Effects of IELLOAR (SEO ID NO:7) Phage and Synthetic Peptides on Tumor Metastasis The effect of IELLQAR (SEQ ID NO:7) phage and peptides on E-selectin mediated tumor metastasis was examined using mouse B16 melanoma cells or human melanoma MeWo cells transfected with fucosyltransferase-III, an enzyme which synthesizes sLe$^x$, as described in Kukowska-Latallo et al., Genes & Develop., 4:1288–1303 (1990). It has been found that the transfected B16 cells express sLe$^x$ on the cell surface and metastasize to the lung in an E-selectin dependent manner. To test whether the heptapeptide sequence IELLQAR (SEQ ID NO:7) could inhibit metastasis in vivo, mice were injected with IELLQAR (SEQ ID NO:7) phage and with B16 cells through a tail vein and assayed for the presence of metastatic foci.

Figure 2:
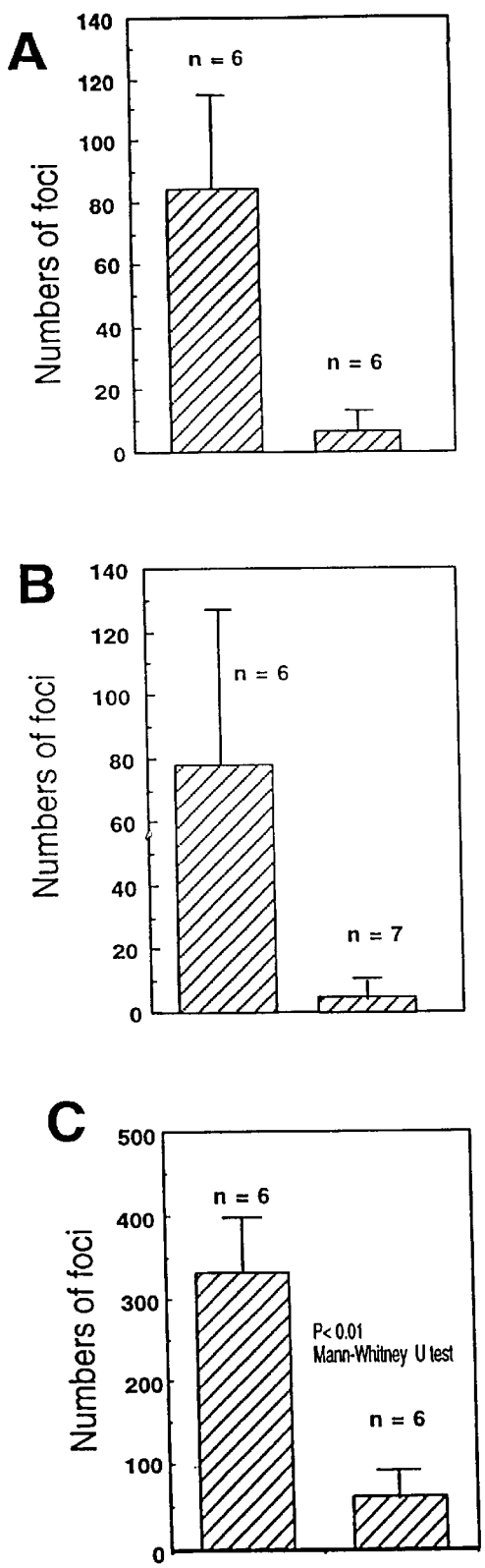
FIG. 2A–2C shows a bar graph illustration of the Metastatic foci appearing in the lung as described in Example III.

Phage ($1 \times 10^8$ transducing units/100 ml/mouse) or peptide (500 mg/100 ml/mouse), each of which was equivalent to an amount 100 times the concentration required to inhibit binding between HL-60 to E-selectin determined by the in vitro assay described above in Example II (FIG. 1F), were injected intravenously into female mice (C57 black) that were 5–6 weeks old. The control phage lacks a consensus heptapeptide. The control peptide used in these experiments is MAPS alanine. After 20 minutes, metastatic tumor cells ($2 \times 10^5$ cells) were administered through a tail vein. After 3 weeks, the numbers of metastatic foci appearing in the lung were counted. The results are shown in FIG. 2.

FIG. 2A quantitates the number of metastatic foci of mouse B16 melanoma formed in the lungs of mice pre-treated with control phage (left bar) or IELLQAR (SEQ ID NO:7) phage (right bar). FIG. 2B quantitates the number of metastatic foci of mouse B16 melanoma formed in lungs of mice pre-treated with control peptide (left bar) or IELLQAR (SEQ ID NO:7) peptide (right bar). FIG. 2C quantitates the number of metastatic foci of human MeWo melanoma formed in lungs of mice pre-treated with control peptide (left bar) or IELLQAR (SEQ ID NO:7) peptide (right bar).

The results indicate that many foci developed in the lungs of animals that received control phage plus B16 cells, whereas none or a few foci were visible in the lungs of the animals that received IELLQAR (SEQ ID NO:7) phage (FIG. 2A). The effect of IELLQAR (SEQ ID NO:7) peptide was assayed in the same manner described above. The multivalent IELLQAR (SEQ ID NO:7) peptide was found to be effective in preventing metastasis (FIG. 2B). The metastases of human melanoma MeWo cells (FIG. 2C) and human lung carcinoma HAL-8 cells to the lung were also inhibited efficiently by the multivalent IELLQAR (SEQ ID NO:7) peptide.

Histochemical Assays

A. Mouse Lung Histochemical Analysis after Intravenous Injection of IELLQAR (SEQ ID NO:7) Peptide Since the metastases analyzed in Example III are dependent on sLe$^x$ expressed on the surface of tumor cells, histochemical analysis was conducted to determine whether an invention peptide inhibited binding of the tumor cells to the lung endothelium by binding to the surface of the vascular endothelium.

Control peptide corresponding to MAPS alanine and IELLQAR (SEQ ID NO:7) peptide were biotinylated with biotin succinamide (Sigma, St. Louis, Mo.) and injected intravenously into mice. One hour after injection, mice were sacrificed, and tissues were examined histochemically using peroxidase conjugated avidin (Cappel, West Chester, Pa.) by the peroxidase method (Vectastatin ABC kit, Vector, Burlingame, Calif.). The results indicate that control peptide does not show any staining on vascular endothelial cells, while IELLQAR (SEQ ID NO:7) peptide is detected on the vascular surface epithelium of the lung. Thus, the IELLQAR (SEQ ID NO:7) peptide has been found to attach to the surface of vascular endothelium cells.

B. Immunohistochemistry of Melanoma Cells in the Lung

Next, the immunohistochemistry in the mouse lung of melanoma cells injected intravenously was assayed. Mice were injected intravenously with either control phage, IELLQAR (SEQ ID NO:7) phage, control peptide, or IELLQAR (SEQ ID NO:7) peptide, followed by injection with B16 melanoma cells. One hour after administering B16 melanoma cells, the lungs were fixed in 4% paraformaldehyde and paraffin sections were prepared. The melanoma cells in the lung were visualized by immunostaining using anti-melanoma HMB45 mouse monoclonal IgG1 antibody (DAKO, Carpinteria, Calif.) by the peroxidase method (Vectastatin ABC kit, Vector, Burlingame, Calif.).

One hour after the administration of B16 melanoma cells, tissue sections of the lungs from mice pre-treated with control phage or control peptide showed that B16 cells had already penetrated the vascular endothelium into the mesenchyme. In contrast, tissue sections from lungs pre-treated with IELLQAR (SEQ ID NO:7) phage or peptide showed that the B16 melanoma cells were non-adherent and appeared apoptotic. These results collectively suggest that the IELLQAR (SEQ ID NO:7) peptide binds in vivo to the ligand binding site of E-selectin at the endothelial surface epithelium and impairs the initial attachment of tumor cells to the endothelium, preventing metastasis in vivo.

While the invention has been described in detail with reference to certain preferred embodiments thereof, it will be understood that modifications and variations are within the spirit and scope of that which is described and claimed.

That which is claimed is:

1. A peptide comprising a heptapeptide selected from the group consisting of:

-I$X_1$L$X_2$Q$X_3$R- (SEQ ID NO:1);

-$X_1$$X_2$LL$X_3$AR- (SEQ ID NO:2); and

-I$X_1$LL$X_2$$X_3$R- (SEQ ID NO:33), wherein said peptide has no more than about 100 amino acids, and wherein said peptide binds to a lectin.

2. The peptide of claim 1, wherein said peptide comprises a heptapeptide selected from the group consisting of:

-I$X_1$L$X_2$QAR- (SEQ ID NO:3);

-I$X_1$LLQ$X_2$R- (SEQ ID NO:4); and

-I$X_1$LL$X_2$AR- (SEQ ID NO:5).

3. The peptide of claim 2, wherein said peptide comprises the amino acid sequence -IXLLQAR- (SEQ ID NO:6).

4. The peptide of claim 3, wherein said peptide comprises an amino acid sequence selected from the group consisting of -IELLQAR- (SEQ ID NO:7), and -ISLLQAR- (SEQ ID NO:8).

5. The peptide of claim 2, wherein said peptide comprises an amino acid sequence selected from the group consisting of -IDLMQAR- (SEQ ID NO:9), -IILLQGR- (SEQ ID NO:10), and -ISLLGAR- (SEQ ID NO:11).

6. The peptide of claim 1, wherein said peptide comprises an amino acid sequence selected from the group consisting of -FSLLDAR- (SEQ ID NO:12), and -IFLLWQR- (SEQ ID NO:34).

7. A composition comprising the peptide of claim 1.

8. The composition of claim 7, wherein said composition is a pharmaceutical composition.

9. A conjugate comprising the peptide of claim 1 linked to a moiety.

10. The conjugate of claim 9, wherein said moiety is a cytotoxic agent or a detectable moiety.

11. The conjugate of claim 9, wherein said cytotoxic agent is a cancer chemotherapeutic agent.

12. The conjugate of claim 9, wherein said moiety is selected from the group consisting of a chambered microdevice, a liposome, a cell, a polypeptide and a virus.

13. A peptide that binds to a member of the mammalian selectin family and inhibits the binding of a carbohydrate to said selectin, wherein said peptide is a hexapeptide selected from the group consisting of:

-$X_1$LL$X_2$$X_3$R- (SEQ ID NO:36),

-$X_1$L$X_2$Q$X_3$R- (SEQ ID NO:14),

-$X_1$L$X_2$QAR- (SEQ ID NO:15),

-$X_1$LL$X_2$AR- (SEQ ID NO:16), and

-$X_1$LLQ$X_2$R- (SEQ ID NO:17).

14. A peptide that binds to a member of the mammalian selectin family and inhibits the binding of a carbohydrate to said selectin, wherein said peptide is a pentapeptide selected from the group consisting of:

-LL$X_1$$X_2$R- (SEQ ID NO:35),

-L$X_1$Q$X_2$R- (SEQ ID NO:24),

-LXQAR- (SEQ ID NO:25),

-LLXAR- (SEQ ID NO:26), and

-LLQXR- (SEQ ID NO:27).

15. A peptide that binds to a member of the mammalian selectin family and inhibits the binding of a carbohydrate to said selectin, wherein said peptide is a heptapeptide selected from the group consisting of:

-I$X_1$L$X_2$Q$X_3$R- (SEQ ID NO:1);

-$X_1$$X_2$LL$X_3$AR- (SEQ ID NO:2); and

-I$X_1$LL$X_2$$X_3$R- (SEQ ID NO:33).

16. The peptide of claim 15, wherein said peptide is a heptapeptide selected from the group consisting of:

-I$X_1$L$X_2$QAR- (SEQ ID NO:3);

-I$X_1$LLQ$X_2$R- (SEQ ID NO:4); and

-I$X_1$LL$X_2$AR- (SEQ ID NO:5).

17. The peptide of claim 1, comprising no more than about 75 amino acids in length.

18. The peptide of claim 1, comprising no more than about 50 amino acids in length.

19. The peptide of claim 1, comprising no more than about 40 amino acids in length.

20. The peptide of claim 1, comprising no more than about 30 amino acids in length.

21. The peptide of claim 1, comprising no more than about 20 amino acids in length.

22. The peptide of claim 1, comprising no more than about 10 amino acids in length.

23. The peptide of claim 1, comprising no more than about 9 amino acids in length.

24. The peptide of claim 1, comprising no more than about 8 amino acids in length.

25. The peptide of claim 1, comprising no more than about 7 amino acids.

26. The peptide of claim 2, comprising no more than about 7 amino acids.

27. The peptide of claim 3, comprising no more than about 7 amino acids.

28. The peptide of claim 4, comprising no more than about 7 amino acids.

29. The peptide of claim 5, comprising no more than about 7 amino acids.

30. The peptide of claim 6, comprising no more than about 7 amino acids.

31. The peptide of claim 13, comprising no more than about 6 amino acids.

32. The peptide of claim 14, comprising no more than about 5 amino acids.

33. The peptide of claim 15, comprising no more than about 7 amino acids.

34. The peptide of claim 16, comprising no more than about 7 amino acids.

* * * * *

SEQUENCE LISTING

```
<160> NUMBER OF SEQ ID NOS: 38

<210> SEQ ID NO 1
<211> LENGTH: 7
<212> TYPE: PRT
<213> ORGANISM: Artificial Sequence
<220> FEATURE:
<221> NAME/KEY: SITE
<222> LOCATION: (2)
<223> OTHER INFORMATION: Xaa is any amino acid
<220> FEATURE:
<221> NAME/KEY: SITE
<222> LOCATION: (4)
<223> OTHER INFORMATION: Xaa is any amino acid
<220> FEATURE:
<221> NAME/KEY: SITE
<222> LOCATION: (6)
<223> OTHER INFORMATION: Xaa is any amino acid
<220> FEATURE:
<223> OTHER INFORMATION: Description of Artificial Sequence: Synthetic
      Construct

<400> SEQUENCE: 1

Ile Xaa Leu Xaa Gln Xaa Arg
 1               5

<210> SEQ ID NO 2
<211> LENGTH: 7
<212> TYPE: PRT
<213> ORGANISM: Artificial Sequence
<220> FEATURE:
<221> NAME/KEY: SITE
<222> LOCATION: (1)..(2)
<223> OTHER INFORMATION: Xaa is any amino acid
<220> FEATURE:
<221> NAME/KEY: SITE
<222> LOCATION: (5)
<223> OTHER INFORMATION: Xaa is any amino acid
<220> FEATURE:
<223> OTHER INFORMATION: Description of Artificial Sequence: Synthetic
      Construct

<400> SEQUENCE: 2

Xaa Xaa Leu Leu Xaa Ala Arg
 1               5

<210> SEQ ID NO 3
<211> LENGTH: 7
<212> TYPE: PRT
<213> ORGANISM: Artificial Sequence
<220> FEATURE:
<221> NAME/KEY: SITE
<222> LOCATION: (2)
<223> OTHER INFORMATION: Xaa is any amino acid
<220> FEATURE:
<221> NAME/KEY: SITE
<222> LOCATION: (4)
<223> OTHER INFORMATION: Xaa is any amino acid
<220> FEATURE:
<223> OTHER INFORMATION: Description of Artificial Sequence: Synthetic
      Construct
```

```
<400> SEQUENCE: 3

Ile Xaa Leu Xaa Gln Ala Arg
 1               5

<210> SEQ ID NO 4
<211> LENGTH: 7
<212> TYPE: PRT
<213> ORGANISM: Artificial Sequence
<220> FEATURE:
<221> NAME/KEY: SITE
<222> LOCATION: (2)
<223> OTHER INFORMATION: Xaa is any amino acid
<220> FEATURE:
<221> NAME/KEY: SITE
<222> LOCATION: (6)
<223> OTHER INFORMATION: Xaa is any amino acid
<220> FEATURE:
<223> OTHER INFORMATION: Description of Artificial Sequence: Synthetic
      Construct

<400> SEQUENCE: 4

Ile Xaa Leu Leu Gln Xaa Arg
 1               5

<210> SEQ ID NO 5
<211> LENGTH: 7
<212> TYPE: PRT
<213> ORGANISM: Artificial Sequence
<220> FEATURE:
<221> NAME/KEY: SITE
<222> LOCATION: (2)
<223> OTHER INFORMATION: Xaa is any amino acid
<220> FEATURE:
<221> NAME/KEY: SITE
<222> LOCATION: (5)
<223> OTHER INFORMATION: Xaa is any amino acid
<220> FEATURE:
<223> OTHER INFORMATION: Description of Artificial Sequence: Synthetic
      Construct

<400> SEQUENCE: 5

Ile Xaa Leu Leu Xaa Ala Arg
 1               5

<210> SEQ ID NO 6
<211> LENGTH: 7
<212> TYPE: PRT
<213> ORGANISM: Artificial Sequence
<220> FEATURE:
<221> NAME/KEY: SITE
<222> LOCATION: (2)
<223> OTHER INFORMATION: Xaa is any amino acid
<220> FEATURE:
<223> OTHER INFORMATION: Description of Artificial Sequence: Synthetic
      Construct

<400> SEQUENCE: 6

Ile Xaa Leu Leu Gln Ala Arg
 1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      Construct

<400> SEQUENCE: 7
```

```
Ile Glu Leu Leu Gln Ala Arg
  1               5
```

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      Construct

<400> SEQUENCE: 8

```
Ile Ser Leu Leu Gln Ala Arg
  1               5
```

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      Construct

<400> SEQUENCE: 9

```
Ile Asp Leu Met Gln Ala Arg
  1               5
```

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      Construct

<400> SEQUENCE: 10

```
Ile Ile Leu Leu Gln Gly Arg
  1               5
```

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      Construct

<400> SEQUENCE: 11

```
Ile Ser Leu Leu Gly Ala Arg
  1               5
```

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      Construct

<400> SEQUENCE: 12

```
Phe Ser Leu Leu Asp Ala Arg
  1               5
```

<210> SEQ ID NO 13
<211> LENGTH: 9
<212> TYPE: PRT
<213> ORGANISM: Artificial Sequence
<220> FEATURE:

<223> OTHER INFORMATION: Description of Artificial Sequence: Synthetic
      Construct

<400> SEQUENCE: 13

Cys Ile Glu Leu Leu Gln Ala Arg Cys
 1               5

<210> SEQ ID NO 14
<211> LENGTH: 6
<212> TYPE: PRT
<213> ORGANISM: Artificial Sequence
<220> FEATURE:
<221> NAME/KEY: SITE
<222> LOCATION: (1)
<223> OTHER INFORMATION: any amino acid
<220> FEATURE:
<221> NAME/KEY: SITE
<222> LOCATION: (3)
<223> OTHER INFORMATION: any amino acid
<220> FEATURE:
<221> NAME/KEY: SITE
<222> LOCATION: (5)
<223> OTHER INFORMATION: any amino acid
<220> FEATURE:
<223> OTHER INFORMATION: Description of Artificial Sequence: Synthetic
      Construct

<400> SEQUENCE: 14

Xaa Leu Xaa Gln Xaa Arg
 1               5

<210> SEQ ID NO 15
<211> LENGTH: 6
<212> TYPE: PRT
<213> ORGANISM: Artificial Sequence
<220> FEATURE:
<221> NAME/KEY: SITE
<222> LOCATION: (1)
<223> OTHER INFORMATION: any amino acid
<220> FEATURE:
<221> NAME/KEY: SITE
<222> LOCATION: (3)
<223> OTHER INFORMATION: any amino acid
<220> FEATURE:
<223> OTHER INFORMATION: Description of Artificial Sequence: Synthetic
      Construct

<400> SEQUENCE: 15

Xaa Leu Xaa Gln Ala Arg
 1               5

<210> SEQ ID NO 16
<211> LENGTH: 6
<212> TYPE: PRT
<213> ORGANISM: Artificial Sequence
<220> FEATURE:
<221> NAME/KEY: SITE
<222> LOCATION: (1)
<223> OTHER INFORMATION: any amino acid
<220> FEATURE:
<221> NAME/KEY: SITE
<222> LOCATION: (4)
<223> OTHER INFORMATION: any amino acid
<220> FEATURE:
<223> OTHER INFORMATION: Description of Artificial Sequence: Synthetic
      Construct

<400> SEQUENCE: 16

Xaa Leu Leu Xaa Ala Arg
 1               5

```
<210> SEQ ID NO 17
<211> LENGTH: 6
<212> TYPE: PRT
<213> ORGANISM: Artificial Sequence
<220> FEATURE:
<221> NAME/KEY: SITE
<222> LOCATION: (1)
<223> OTHER INFORMATION: any amino acid
<220> FEATURE:
<221> NAME/KEY: SITE
<222> LOCATION: (5)
<223> OTHER INFORMATION: any amino acid
<220> FEATURE:
<223> OTHER INFORMATION: Description of Artificial Sequence: Synthetic
      Construct

<400> SEQUENCE: 17

Xaa Leu Leu Gln Xaa Arg
 1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      Construct

<400> SEQUENCE: 18

Ser Leu Leu Gln Ala Arg
 1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      Construct

<400> SEQUENCE: 19

Asp Leu Met Gln Ala Arg
 1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      Construct

<400> SEQUENCE: 20

Ile Leu Leu Gln Gly Arg
 1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      Construct

<400> SEQUENCE: 21

Ser Leu Leu Gln Ala Arg
 1               5

<210> SEQ ID NO 22
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      Construct

<400> SEQUENCE: 22

Ser Leu Leu Asp Ala Arg
 1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      Construct

<400> SEQUENCE: 23

Glu Leu Leu Gln Ala Arg
 1               5

<210> SEQ ID NO 24
<211> LENGTH: 5
<212> TYPE: PRT
<213> ORGANISM: Artificial Sequence
<220> FEATURE:
<221> NAME/KEY: SITE
<222> LOCATION: (2)
<223> OTHER INFORMATION: any amino acid
<220> FEATURE:
<221> NAME/KEY: SITE
<222> LOCATION: (4)
<223> OTHER INFORMATION: any amino acid
<220> FEATURE:
<223> OTHER INFORMATION: Description of Artificial Sequence: Synthetic
      Construct

<400> SEQUENCE: 24

Leu Xaa Gln Xaa Arg
 1               5

<210> SEQ ID NO 25
<211> LENGTH: 5
<212> TYPE: PRT
<213> ORGANISM: Artificial Sequence
<220> FEATURE:
<221> NAME/KEY: SITE
<222> LOCATION: (2)
<223> OTHER INFORMATION: any amino acid
<220> FEATURE:
<223> OTHER INFORMATION: Description of Artificial Sequence: Synthetic
      Construct

<400> SEQUENCE: 25

Leu Xaa Gln Ala Arg
 1               5

<210> SEQ ID NO 26
<211> LENGTH: 5
<212> TYPE: PRT
<213> ORGANISM: Artificial Sequence
<220> FEATURE:
<221> NAME/KEY: SITE
<222> LOCATION: (3)
<223> OTHER INFORMATION: any amino acid
<220> FEATURE:
<223> OTHER INFORMATION: Description of Artificial Sequence: Synthetic
      Construct
```

```
<400> SEQUENCE: 26

Leu Leu Xaa Ala Arg
 1               5

<210> SEQ ID NO 27
<211> LENGTH: 5
<212> TYPE: PRT
<213> ORGANISM: Artificial Sequence
<220> FEATURE:
<221> NAME/KEY: SITE
<222> LOCATION: (4)
<223> OTHER INFORMATION: any amino acid
<220> FEATURE:
<223> OTHER INFORMATION: Description of Artificial Sequence: Synthetic
      Construct

<400> SEQUENCE: 27

Leu Leu Gln Xaa Arg
 1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      Construct

<400> SEQUENCE: 28

Leu Leu Gln Ala Arg
 1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      Construct

<400> SEQUENCE: 29

Leu Met Gln Ala Arg
 1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      Construct

<400> SEQUENCE: 30

Leu Leu Gly Ala Arg
 1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      Construct

<400> SEQUENCE: 31

Leu Leu Asp Ala Arg
 1               5
```

```
<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      Construct

<400> SEQUENCE: 32

Leu Leu Gln Gly Arg
 1               5

<210> SEQ ID NO 33
<211> LENGTH: 7
<212> TYPE: PRT
<213> ORGANISM: Artificial Sequence
<220> FEATURE:
<221> NAME/KEY: SITE
<222> LOCATION: (2)
<223> OTHER INFORMATION: Xaa = any amino acid
<220> FEATURE:
<221> NAME/KEY: SITE
<222> LOCATION: (5)..(6)
<223> OTHER INFORMATION: Xaa = any amino acid
<220> FEATURE:
<223> OTHER INFORMATION: Description of Artificial Sequence: Synthetic
      Construct

<400> SEQUENCE: 33

Ile Xaa Leu Leu Xaa Xaa Arg
 1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      Construct

<400> SEQUENCE: 34

Ile Phe Leu Leu Trp Gln Arg
 1               5

<210> SEQ ID NO 35
<211> LENGTH: 5
<212> TYPE: PRT
<213> ORGANISM: Artificial Sequence
<220> FEATURE:
<221> NAME/KEY: SITE
<222> LOCATION: (3)..(4)
<223> OTHER INFORMATION: Xaa = any amino acid
<220> FEATURE:
<223> OTHER INFORMATION: Description of Artificial Sequence: Synthetic
      Construct

<400> SEQUENCE: 35

Leu Leu Xaa Xaa Arg
 1               5

<210> SEQ ID NO 36
<211> LENGTH: 6
<212> TYPE: PRT
<213> ORGANISM: Artificial Sequence
<220> FEATURE:
<221> NAME/KEY: SITE
<222> LOCATION: (1)
<223> OTHER INFORMATION: Xaa = any amino acid
<220> FEATURE:
<221> NAME/KEY: SITE
```

-continued

```
<222> LOCATION: (4)..(5)
<223> OTHER INFORMATION: Xaa = any amino acid
<220> FEATURE:
<223> OTHER INFORMATION: Description of Artificial Sequence: Synthetic
      Construct

<400> SEQUENCE: 36

Xaa Leu Leu Xaa Xaa Arg
  1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      Construct

<400> SEQUENCE: 37

Phe Leu Leu Trp Gln Arg
  1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      Construct

<400> SEQUENCE: 38

Phe Ala Gln Leu Asp Trp His
  1               5
```